US006581400B2

(12) United States Patent
Augustine et al.

(10) Patent No.: US 6,581,400 B2
(45) Date of Patent: *Jun. 24, 2003

(54) APPARATUS, SYSTEM, AND METHOD FOR CONVECTIVELY AND EVAPORATIVELY COOLING A HEAD

(75) Inventors: Scott D. Augustine, Bloomington, MN (US); Paul Anthony Iaizzo, White Bear Lake, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/262,405

(22) Filed: Sep. 30, 2002

(65) Prior Publication Data

US 2003/0029182 A1 Feb. 13, 2003

Related U.S. Application Data

(63) Continuation of application No. 09/606,300, filed on Jun. 28, 2000, which is a continuation of application No. 09/176,477, filed on Oct. 20, 1998, now Pat. No. 6,119,474, which is a continuation of application No. 08/918,308, filed on Aug. 26, 1997, now Pat. No. 5,860,292.

(51) Int. Cl.⁷ .......................... F25D 23/12; F28D 5/00; A61F 7/00

(52) U.S. Cl. .................. 62/259.3; 62/314; 607/107

(58) Field of Search ............................ 62/255.3, 314, 62/304; 607/104, 107; 165/46

(56) References Cited

U.S. PATENT DOCUMENTS

| 1,907,709 | A | * | 5/1933 | Barrow ............................ 2/171 |
| 3,468,299 | A | * | 9/1969 | D'Amato ....................... 126/204 |
| 3,696,814 | A | * | 10/1972 | Umemoto ..................... 607/110 |
| 4,572,188 | A | * | 2/1986 | Augustine et al. ............ 128/380 |
| 4,597,757 | A | * | 7/1986 | Ruderian ....................... 604/291 |
| 4,744,106 | A | * | 5/1988 | Wang .................................. 2/7 |
| 4,777,802 | A |   | 10/1988 | Feher |
| 5,014,355 | A | * | 5/1991 | Vollenweider, II ................ 2/79 |
| 5,062,424 | A |   | 11/1991 | Hooker |
| 5,106,373 | A | * | 4/1992 | Augustine et al. ............ 614/113 |
| 5,300,101 | A |   | 4/1994 | Augustine et al. |
| 5,324,320 | A |   | 6/1994 | Augustine et al. |
| 5,336,250 | A |   | 8/1994 | Augustine |
| 5,350,417 | A |   | 9/1994 | Augustine |
| 5,405,371 | A |   | 4/1995 | Augustine et al. |
| 5,497,633 | A |   | 3/1996 | Jones et al. |
| 5,545,196 | A | * | 8/1996 | Falk ............................. 607/105 |
| 5,564,124 | A | * | 10/1996 | Elsherif et al. ................... 2/69 |
| 5,588,968 | A | * | 12/1996 | Sternlicht .................... 607/107 |
| 5,609,619 | A | * | 3/1997 | Pompei ....................... 607/104 |
| 5,652,987 | A | * | 8/1997 | Fujita ............................ 5/726 |
| 5,715,533 | A | * | 2/1998 | Stein ................................. 2/7 |
| 5,860,292 | A | * | 1/1999 | Augustine et al. .......... 62/259.3 |
| 6,119,474 | A | * | 9/2000 | Augustine et al. .......... 62/259.3 |
| 6,487,871 | B1 | * | 12/2002 | Augustine et al. .......... 62/259.3 |

* cited by examiner

*Primary Examiner*—William C. Doerrler
(74) *Attorney, Agent, or Firm*—Gray Cary Ware & Freidenrich; Terrance A. Meador

(57) ABSTRACT

An apparatus is disclosed for convectively and evaporatively cooling a patient's head. The apparatus includes an upper sheet and a base sheet that are attached at a plurality of locations to form a convective device adaptable to the patient's head. The base sheet includes a plurality of apertures that direct an inflating medium from the convective device toward the patient's head. The base sheet also supports an evaporative cooling element that distributes and delivers a cooling fluid to the patient's head. The fluid is evaporated from the patient's head by the inflating medium exhausted from the convective device. The evaporative cooling element may be constructed in a variety of configurations and may circulate a variety of fluids, which may be pressurized or unpressurized. In operation, an air blower, that may also include a compressor for selectively delivering room temperature or cooled air to the apparatus, is connected to the convective device. The blower delivers air, under pressure, to an inlet opening in the convective device. The pressurized air is distributed throughout the convective device and flows to the patient's head through the apertures in the base sheet.

40 Claims, 8 Drawing Sheets

APPARATUS, SYSTEM, AND METHOD FOR CONVECTIVELY AND EVAPORATIVELY COOLING A HEAD

This application is a continuation of U.S. patent application Ser. No. 09/606,300, filed Jun. 28, 2000, which is a continuation of U.S. patent application Ser. No. 09/176,477, filed Oct. 20, 1998, now U.S. Pat. No. 6,119,474, which is a continuation of U.S. patent application Ser. No. 08/918,308, filed Aug. 26, 1997, now U.S. Pat. No. 5,860,292.

BACKGROUND OF THE INVENTION

1. Field of the Invention

This invention relates generally to convective devices used in a medical setting to deliver a bath of thermally-controlled gaseous medium, such as air, to a patient's head.

2. Description of the Related Art

Thermal blanket prior art is disclosed in commonly-assigned U.S. Pat. No. 4,572,188 entitled "AIRFLOW COVER FOR CONTROLLING BODY TEMPERATURE" and U.S. Pat. No. 5,405,371 entitled "THERMAL BLANKET". These two patents describe thermal blankets which include a plurality of communicating inflatable chambers. In these blankets, apertures are formed through blanket base sheets. These apertures open through the base sheets into the chambers. When inflated with warmed air, the pressure of the air in the chambers causes the air flow cover to inflate. The apertures exhaust the warmed air through the base sheets, and the warmed air is contained between the base sheets and the patients. Therefore, these thermal blankets create an ambient environment about the patient, the thermal characteristics of which are determined by the temperature and pressure of the gaseous inflating medium.

Temperature control in humans has important medical consequences. The human body has evolved over several million years to maintain its core temperature within a very narrow range. Thermoregulatory responses such as vasoconstriction, vasodilatation, shivering or sweating occur in response to core body temperature changes as small as +/−0.1° C. Human cellular functions, biochemical reactions and enzymatic reactions are optimized within this narrow temperature range.

The prior art thermal blankets address the problem of warming a patient in order to treat hypothermia (a core temperature that is less than normal) such as might occur operatively or post-operatively. These thermal blankets have proven themselves to be extremely useful and efficient in the treatment of patients whose core body temperatures might otherwise become undesirably low either during or after a medical procedure, such as surgery.

However, there are circumstances under which a patient should be cooled rather than warmed in order to treat hyperthermia (a core temperature that is greater than normal). Hyperthermia may result from environmental heat stress or from illness. Otherwise normal individuals may suffer hyperthermia when their natural cooling mechanisms, such as sweating, are overwhelmed during heavy physical work in a hot environment. This is usually associated with relatively inadequate fluid consumption that results in inadequate sweating. Heat stress disorders, categorized in ascending order of severity include: heat cramps, heat syncope, heat exhaustion and heat stroke. Normally, a person will voluntarily stop working well before the onset of heat exhaustion, but competitive athletes or military personnel may push themselves beyond this limit.

Hyperthermia may also be caused by fever associated with illness. Such fever has many causes, including: infection, tumor necrosis, thyroid storm, malignant hyperthermia or brain injury. Brain injuries that cause hyperthermia usually involve the hypothalamus, and may be caused by tumors, stroke, head injury or ischemic brain injury due to cardiac arrest.

The physiologic consequences of hyperthermia span a spectrum of severity with fluid and electrolyte imbalances, increased cellular metabolic rates, and cognitive impairment being at the low end. In the mid-spectrum, motor skill impairment, loss of consciousness and seizures occur. At the high end, the individual suffers irreversible cellular injury, especially of the highly metabolic brain and liver cells, and then finally organ failure and death. Hyperthermia is a thus a condition that, depending on its severity, may require immediate cooling treatment to return the patient's core temperature to normal.

Cooling treatment may also have other important uses. There is a growing body of evidence suggesting that in some situations, mild-to-moderate hypothermia may provide beneficial protection against injury. The protective benefit of hypothermia has been shown when the blood flow to all or part of the brain is interrupted. Brain ischemia due to an interruption of the blood flow may occur during cardiac arrest, surgery on the blood vessels of the brain, stroke, traumatic brain injury or open heart surgery. Cooling the brain before or in some cases after these events occur seems to be protective, and decreases the severity of the ultimate brain damage.

Various apparatus and techniques have been used over the centuries to cool the human body. Cooling technologies can be generally categorized as: conductive, convective, or evaporative. While many technologies have been tried, all are limited in the clinical setting by lack of practicality, difficulty of use, ineffectiveness, and/or excessive power consumption.

Conductive cooling is very effective when accomplished by packing a hyperthermic person in ice, or immersing the person in cool, or even cold, water. While ice is an effective cooling agent, it is painful to the patient, can damage the skin, is frequently not available in large quantities, and is not practical for long term use. Water baths are also effective, but not practical for the comatose or intensive care patient, or for long term use. A less effective, but commonly used, method of conductive cooling involves placing the person on, and/or under, a cold water circulating mattress and/or cover. These devices have chambers with circulating water therein. The water cools the surfaces of the device, which in turn removes heat from the patient wherever the surfaces thermally contact the patient's skin. These devices are generally uncomfortable and heavy, and their thermal contact is frequently inefficient because they are not precisely shaped to the body surface.

Convective cooling consists of blowing room temperature air, or cooled air onto the patient. Convective cooling is the least effective method of cooling, from a thermodynamic point of view. Room temperature air can be blown very inexpensively with a fan. However, its cooling effectiveness is severely limited if the patient is not sweating. Cooled air can be made with a traditional compression or heat-pump air conditioner, or with thermoelectric cooling. Cooled air has also been generated for centuries using the so called "swamp cooler" principle of vaporizing water into the air stream. The water evaporates into the air, thus cooling the air. The cooled air is then applied to a person.

An example of such a cooler is shown in U.S. Pat. No. 5,497,633 entitled "EVAPORATIVE COOLING UNIT" by Jones et al. Once the air is cooled by any of these technologies, it can be delivered to a person by generally cooling the environment around the person, such as cooling the air in a room. For more efficient convective cooling utilizing less energy, the cooled air can be delivered to a person more effectively by confining the cooling to only the person. This can be accomplished using a convective thermal blanket such as shown in U.S. Pat. Nos. 4,572,188 or 5,405,371, referred to above and incorporated herein by reference. Another convective thermal blanket is shown in U.S. Pat. No. 4,777,802 entitled "BLANKET ASSEMBLY AND SELECTIVELY ADJUSTABLE APPARATUS FOR PROVIDING HEATED OR COOLED AIR THERETO" by Feher. Confined convective cooling has also been shown in the form of a jacket-like device in U.S. Pat. No. 5,062,424 entitled "PORTABLE APPARATUS FOR RAPID REDUCTION OF ELEVATED BODY CORE TEMPERATURE" by Hooker.

Convective cooling removes the stress of environmental heat, but is minimally effective in active cooling. This limited thermodynamic effectiveness is particularly evident when trying to cool patients with fevers. Generally, in order to be cooled by convection, the patients must be anesthetized and paralyzed to prevent heat producing shivering. Further, the thermodynamic inefficiency of convective cooling causes this method of cooling to use considerable electrical power and generate considerable waste heat, both of which can be a problem in the emergency or intensive care situation.

Evaporative cooling is the thermodynamic basis of the highly efficient sweating response. Each gram of water that evaporates extracts 540 calories of heat from the skin of the body being cooled. Because of the very large heat of vaporization of water, large amounts of heat are removed from the body by evaporating relatively small amounts of water. Evaporative cooling has been practiced since the beginning of mankind, simply by wetting the skin or clothing, and letting the wetting agent evaporate. Evaporative cooling is used even today in hospitals, in the form of sponge baths, where the patient is wetted with water, and allowed to dry by evaporation. Sometimes a fan will be blown on the patient to increase the rate of evaporation. While this method of cooling is clearly effective, it is labor intensive, messy, requires the patient to be totally exposed, and is generally not practical for prolonged cooling. Finally, the effectiveness of evaporative cooling is severely limited in high humidity environments.

Therefore, there is a need for a temperature control device, and particularly a thermal blanket, that can accommodate a patient who requires treatment for hyperthermia or requires cooling as an injury prevention mechanism. What is required is an inexpensive covering that cools a patient rapidly and efficiently in a clinical setting, yet which may be easily and conveniently used by medical personnel.

SUMMARY OF THE INVENTION

In accordance with certain objectives of this invention, and to overcome the limitations of the prior art, an apparatus is provided that compounds convection with evaporation to cool a patient. The apparatus includes an inflatable thermal blanket including an upper sheet and a base sheet that are attached at a plurality of locations to form an inflatable structure. The base sheet includes a plurality of apertures that exhaust an inflating medium from the inflatable structure toward the patient. An air blower that may also include a compressor for selectively delivering room temperature, or cooled, air to the thermal blanket, delivers air, under pressure, to an inlet opening in the inflatable thermal blanket. The pressurized air is distributed within the inflatable structure, and flows to the patient through the apertures in the base sheet. The base sheet supports a fluid delivery element that directs a cooling fluid onto the patient. The fluid is evaporated by the inflating medium exhausted from the inflatable structure. The fluid delivery element may be constructed in a variety of configurations and may circulate a variety of fluids, which may be pressurized or unpressurized.

The inflatable thermal blanket is configured to cover one or more portions of a patient's body. In a first preferred embodiment, the thermal blanket covers all of the patient's body except for the head. In an alternative embodiment, a specially designed thermal blanket is constructed to cover only the patient's head.

It is therefore a primary object of the invention to provide a convenient, inexpensive and effective means for rapidly cooling a body (human or animal).

It is a further object of the invention to provide a device for cooling a body both convectively and evaporatively.

It is a further object to provide such cooling in an inexpensive inflatable thermal blanket which can be used with existing inflatable thermal blanket equipment.

The foregoing, together with other objects, features and advantages of this invention, will become more apparent when referring to the following specification, claims and the accompanying drawings.

BRIEF DESCRIPTION OF THE PREFERRED EMBODIMENT

For a more complete understanding of this invention, reference is now made to the following detailed description of the embodiments as illustrated in the accompanying drawing, wherein.

DETAILED DESCRIPTION OF THE PREFERRED EMBODIMENT

This invention is represented by embodiments set forth in the following description, and illustrated in the figures, in which like numbers represent the same or similar elements. While this invention is described in terms of an exemplary embodiment, it will be appreciated by those skilled in the art that variations may be accomplished in view of these teachings, without deviating from the spirit or scope of the invention.

Effective patient cooling in a clinical setting is achieved by providing an inflatable thermal blanket that joins an air delivery system for providing a convective cooling component with a fluid delivery apparatus for providing an evaporative. Cooling component. It has been found that combining evaporative cooling with convective cooling with an inflatable thermal blanket dramatically increases the cooling effectiveness of the convective cooling, while making the evaporative cooling convenient and practical, even for prolonged use. The inflatable thermal blankets disclosed herein maximize the positive features of convective and evaporative cooling while minimizing the negative features of each.

Figure 1:
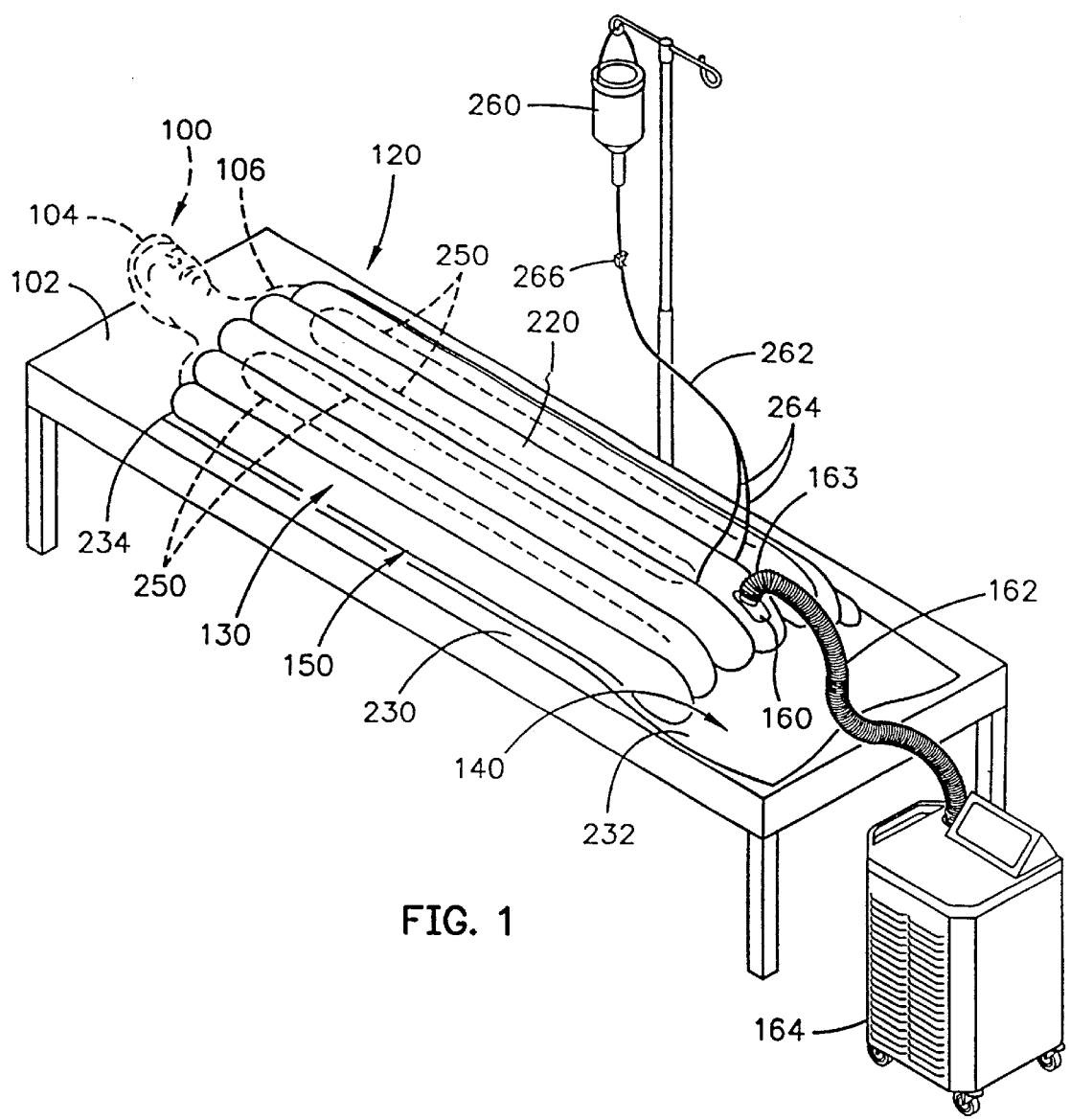
FIG. 1 is a perspective view of a patient and an inflatable thermal blanket according to the invention, deployed with forced-air pump that supplies air to the thermal blanket, and a fluid supply system for delivering an evaporative cooling fluid to the thermal blanket.
Figure 3:
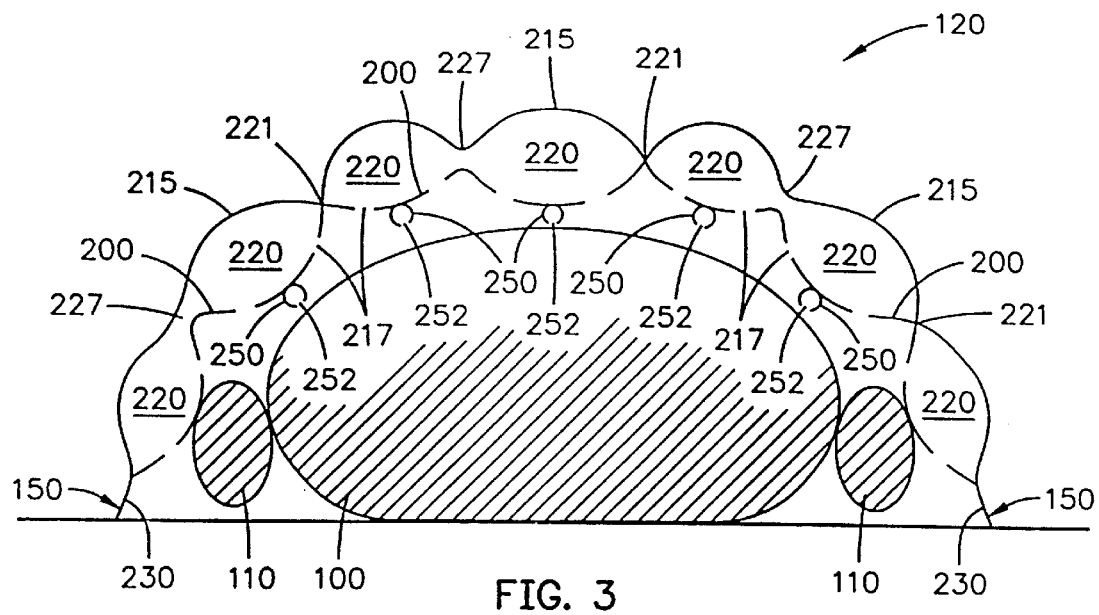
FIG. 3 is a diagrammatic cross-sectional view of the patient and inflatable thermal blanket of FIG. 1, showing one alternative lateral placement arrangement for components of a fluid delivery apparatus.
Figure 4:
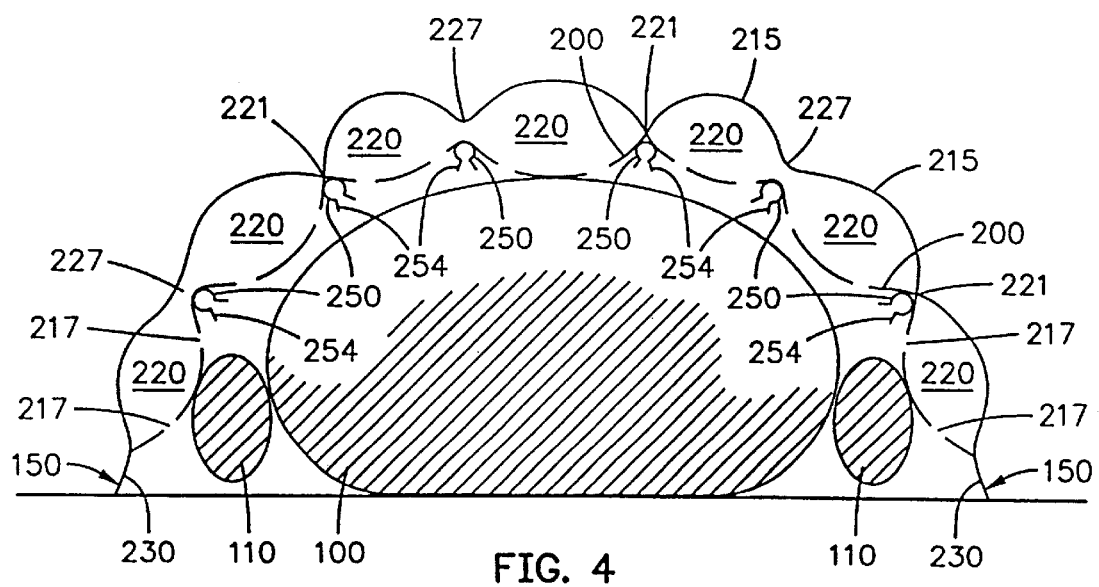
FIG. 4 is another diagrammatic cross-sectional view of the patient and inflatable thermal blanket of FIG. 1, showing another alternative lateral placement arrangement for components of a fluid delivery apparatus.

FIG. 1 illustrates a patient 100 in a prone position on an examination or operating table 102. The table 102 may be in doctor's office, in an out-patient facility associated with a hospital facility, or any other suitable location. The patient 100 is illustrated with his head 104 and shoulders 106 lying flat and supported on the table 102 (along with the remainder of the patient's body). As shown in FIGS. 3 and 4, the patient's arms 110 lie at the patient's side.

An inflatable thermal blanket indicated by reference numeral 120, and having convective cooling and evaporative cooling components, is shown covering all of the patient's body, except for the head 104 and shoulders 106. The inflatable thermal blanket 120 includes an inflatable section 130 surrounded by a non-inflatable section that includes a foot drape 140 and side edges 150. A head drape could also be provided, as could one or more non-inflatable recesses in the inflatable portion 130 to facilitate unrestricted viewing of, and access to, selected areas of the patient 100.

Further, FIG. 1 is not meant to suggest limitation of the invention to an inflatable thermal blanket that covers substantially all of a patient's trunk and limbs. It could also be embodied in an arrangement that uses an inflatable thermal blanket that is shaped and deployed over portions of the patient's body, as well as over one, or fewer than all of the patient's limbs. In this regard, for example, reference is given to U.S. Pat. No. 5,405,371, which describes inflatable thermal blankets that cover the outstretched arms and upper chest, and the lower extremities of a person. Other configurations are illustrated in U.S. Pat. Nos. 5,300,101; 5,324,320; 5,336,250; and 5,350,417.

Returning to FIG. 1, the inflatable section 130 includes an inlet 160 through which a flow of temperature-controlled air is received to inflate the inflatable thermal blanket. The flow of air is provided by an airhose 162 from a forced-air unit 164. The forced-air unit 164 minimally includes a blower system powered by an electric motor or the like for delivering a flow of air. The blower system preferably has variable air speed control capability and may have air temperature control capability. Optionally, for additional cooling effectiveness, especially in hot and humid environments, an air cooling unit or dehumidifying unit could be included in the forced-air unit. Alternatively, the air cooling unit or dehumidifying unit may be separate from the forced-air unit, in which case it could be interposed between the forced air-unit and the airhose 162. Cooled air increases the efficiency of the convective cooling component of the blanket 120. Dehumidified air increases the efficiency of the evaporative cooling component of the blanket. Cooled, dehumidified air therefore optimizes patient cooling.

The inlet 160 in the inflatable section 130 may be provided with a cuff or other conventional connector adapted to receive and retain a nozzle 163 of the airhose 162. Using this configuration, pressurized air can flow through the airhose 162 into the inflatable section 130.

The inflatable thermal blanket 120 of this invention may be constructed by modifying a commercially available inflatable thermal blanket of the type which is known in the art, including BAIR HUGGER® Thermal Blankets from Augustine Medical, Inc., Eden Prairie Minn. Alternatively, the inflatable thermal blanket 120 could be constructed using methods and materials that are known for making similar products. One example of construction details suitable for making the inflatable thermal blanket of this invention is found in commonly-assigned U.S. Pat. No. 5,405,371.

Figure 2:
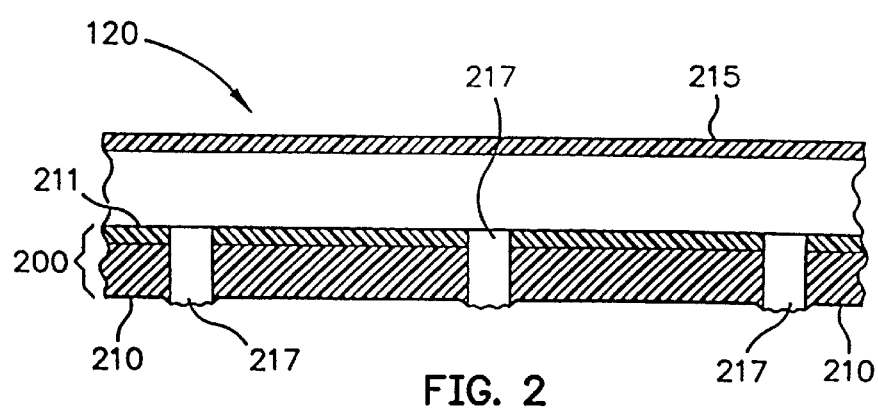
FIG. 2 is a partial cross-sectional view taken through an inflatable portion of the inflatable thermal blanket of FIG. 1.

With reference now to FIGS. 1 and 2, the inflatable thermal blanket 120 is assembled from a base sheet 200 having a laminated structure in which a bottom layer 210 comprises a fibrous, preferably non-woven, structure composed of synthetic or natural materials. A top layer 211, comprising a sheet of synthetic material, is disposed on and laminated to a surface of the bottom layer 210. For example, the bottom layer 210 may be a non-woven, hydroentangled polyester material and the top layer may include a polypropylene film that is extrusion-coated on to the polyester layer. According to a first alternative, the bottom layer 210 may comprise a nonwoven, paper-based material to which a top layer including either a polyethylene or a polypropylene film has been glue laminated. According to a second alternative, the bottom layer may comprise a single layer of fibrous material. To form an inflatable structure that may include one or more inflatable chambers 220, an upper sheet 215 of material is attached at a plurality of locations to the top layer 211. Preferably, the upper sheet 215 comprises the same material as the top layer 211 of the base sheet 200. The upper sheet 215 is attached to the top layer 211 in the preferred embodiment in a continuously-running web process that includes stations at which the upper sheet 215 is heat-bonded to the top layer 211 to form the inflatable and non-inflatable sections of the inflatable thermal blanket 150. The inflatable chambers 220 are shown in FIGS. 1, 3 and 4 as having a generally elongate tubular shape, although such chambers and shapes are not necessary to the invention. The inflatable chambers 220 are formed by discontinuous elongate heat seals extending longitudinally along the blanket

120. FIGS. 3 and 4 show a cross-sectional view of the elongate heat seals. These heat seals are shown as having sealed portions 221 and unsealed portions 227. At the sealed portions 221 of the discontinuous elongate heat seals, the top layer 211 of the base sheet 200 is bonded to the upper sheet 215 in an elongate, air impermeable seam. Where the discontinuities 227 occur, air may circulate laterally between the inflatable chambers. These discontinuities provide communication between the inflatable chambers, permitting pressurized air to circulate from the inlet 160 to, and through, the inflatable chambers 220. It should be understood that the inflatable structure could be formed by a plurality of stake-point seals, or by longer elongate seals. The plurality of apertures 217 that open through the base sheet 200 exhaust pressurized air from the inflatable chambers 220 underneath the inflatable thermal blanket 120 to bathe the patient 100 in a cooling ambient atmosphere.

Continuous, air impervious seals 230 are shown in FIGS. 1, 3 and 4 along the sides of the inflatable thermal blanket 120. Continuous, air impervious seals 232 and 234 also extend transversely at the foot end and the head end of the blanket 120, respectively. These seals form the one or more uninflatable sections of the inflatable thermal blanket 150. These uninflatable sections function essentially as drapes that maintain an ambient atmosphere beneath the inflatable thermal blanket. As FIGS. 1, 3 and show, there are two, parallel continuous, air-impervious edge seals 230 that are near the respective sides of the inflatable thermal blanket and two continuous, air-impervious end seals 232 and 234 at either end of the inflatable thermal blanket. The perimeter of the inflatable thermal blanket 120 is therefore sealed by a continuous, air-impervious seal comprising the seals 230, 232 and 234.

The invention further includes an evaporative cooling element comprising a fluid distribution apparatus. The fluid distribution apparatus distributes fluid over, and delivers it to, various areas, portions, or limbs of a patient's body. The fluid distribution apparatus includes one or more fluid delivery channels or conduits 250 mounted to the underside of the base sheet 200. Preferably, the conduits 250 are attached to the inflatable thermal blanket 120 in areas of the blanket that correspond to areas of the patient's body that are to be evaporatively cooled. In FIG. 1, the conduits 250 are shown extending from the patient's chest area to the patient's lower legs. In FIG. 3, the conduits 250 are attached to the underside of the inflatable thermal blanket 120 below central portions of the inflatable section 130. In FIG. 4, the conduits 250 are attached to the underside of the inflatable thermal blanket 120 below the discontinuous elongate heat seals. One example of a fluid conduit would be a length of approximately ⅛ inch internal diameter PVC tubing, similar to standard IV (intravenous) tubing.

The fluid conduits 250 deliver fluid to the patient 100 through a plurality of orifices 252, which are formed intermittently along the length of each conduit in the walls thereof. The orifices 252 allow fluid to be delivered to a selected area or areas of the patient 100. As shown in FIG. 3, the orifices 252 may be holes, or they may be slits, or any other type of perforations that allow the fluid to pass through the wall of the conduits 250, and be deposited onto the body surface below. Alternatively, as shown in FIG. 4, the orifices may be formed as nozzles 254 that allow the fluid to be sprayed through the wall of the conduits 250, on the body surface below. Additionally, the orifices 252 may include openings 256 in the ends of the conduits 250.

As shown in FIG. 1, the fluid distribution apparatus includes a fluid reservoir 260 connected to the conduits 250, via an inlet line 262, and an inlet manifold 264. The fluid reservoir 260 is preferably a collapsible plastic bag, identical to the currently-used IV fluid containers. Alternatively, bottled fluid or a continuous supply from a water system could be used. The inlet line 262 is preferably made from fluid supply tubing such as standard IV tubing with standard Luer connectors at each end. A valve 266 is provided in inlet line 262 to allow an operator to control the flow rate of the fluid. The inlet manifold 264, which distributes fluid among the conduits, can be formed in a variety of ways.

Figure 5:
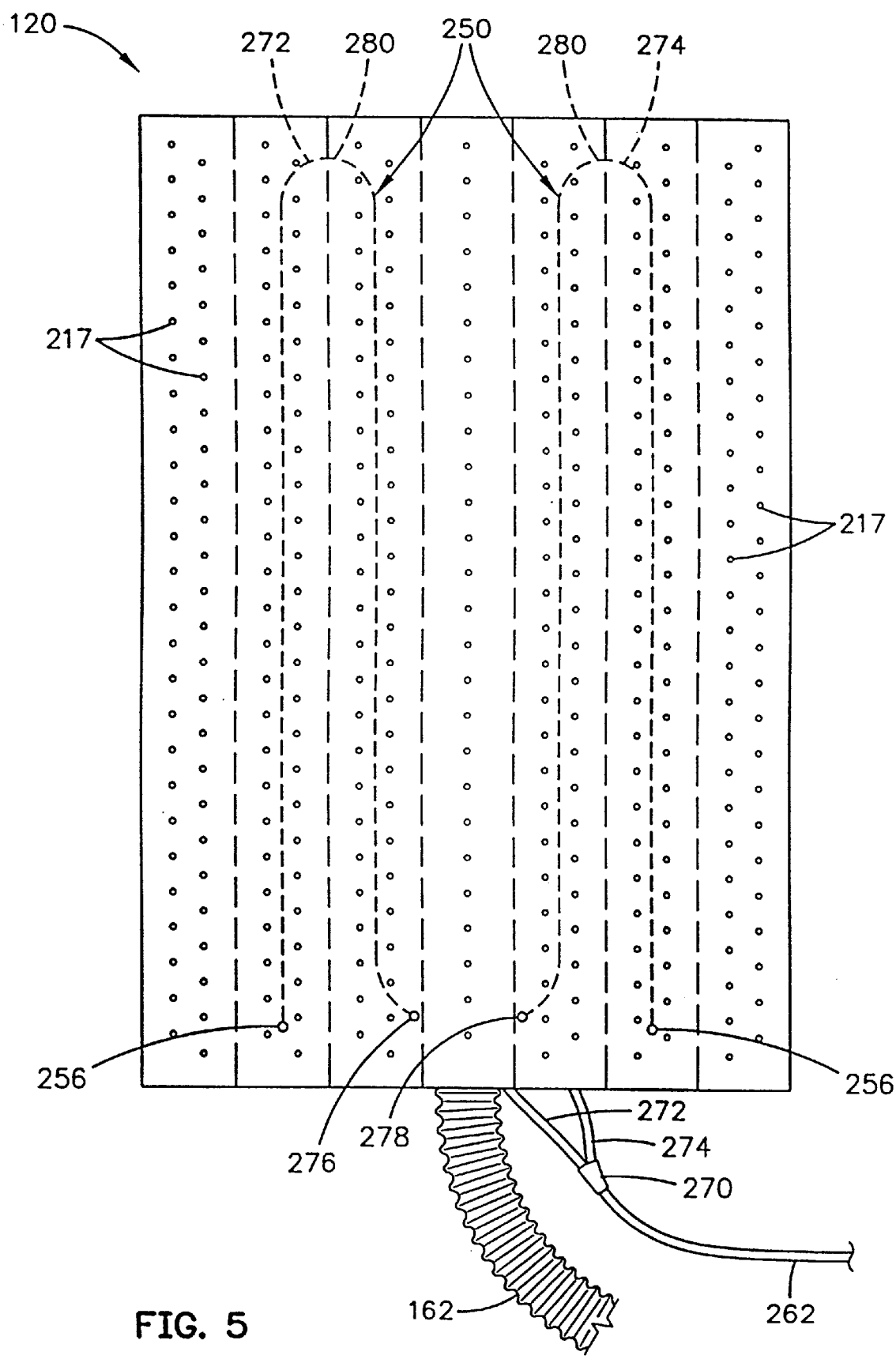
FIG. 5 is a bottom view of the inflatable thermal blanket of FIG. 1, showing one alternative two-dimensional placement for components of a fluid delivery apparatus and also showing one alternative manifold therefor.

FIG. 5 illustrates the inlet manifold as a Y-connection coupler 270 that is attached, at its upstream side, to the end of the inlet line 262. FIG. 5 also illustrates an alternative pattern for the conduits 250, in which two conduits 272 and 274 made from small bore plastic tubing are attached to the downstream side of the coupler 270. These conduits extend from the upper side of the inflatable thermal blanket 120 to the underside thereof through respective holes 276 and 278 that are formed in adjacent ones of the seals that join the upper and base sheets of the inflatable thermal blanket 120. The conduits 272 and 274 are attached to the underside of the inflatable thermal blanket 120 in a serpentine pattern. In the configuration shown in FIG. 5, the orifices 280 of the conduits are oriented to wet the entire body of the patient 100 except the head area. It should also be understood that the conduits could be oriented to wet only selected parts of the body. As shown in FIG. 5, the numerous air apertures 217 will direct evaporative air to all portions of the patient's body where fluid is delivered by the conduits.

Figure 6:
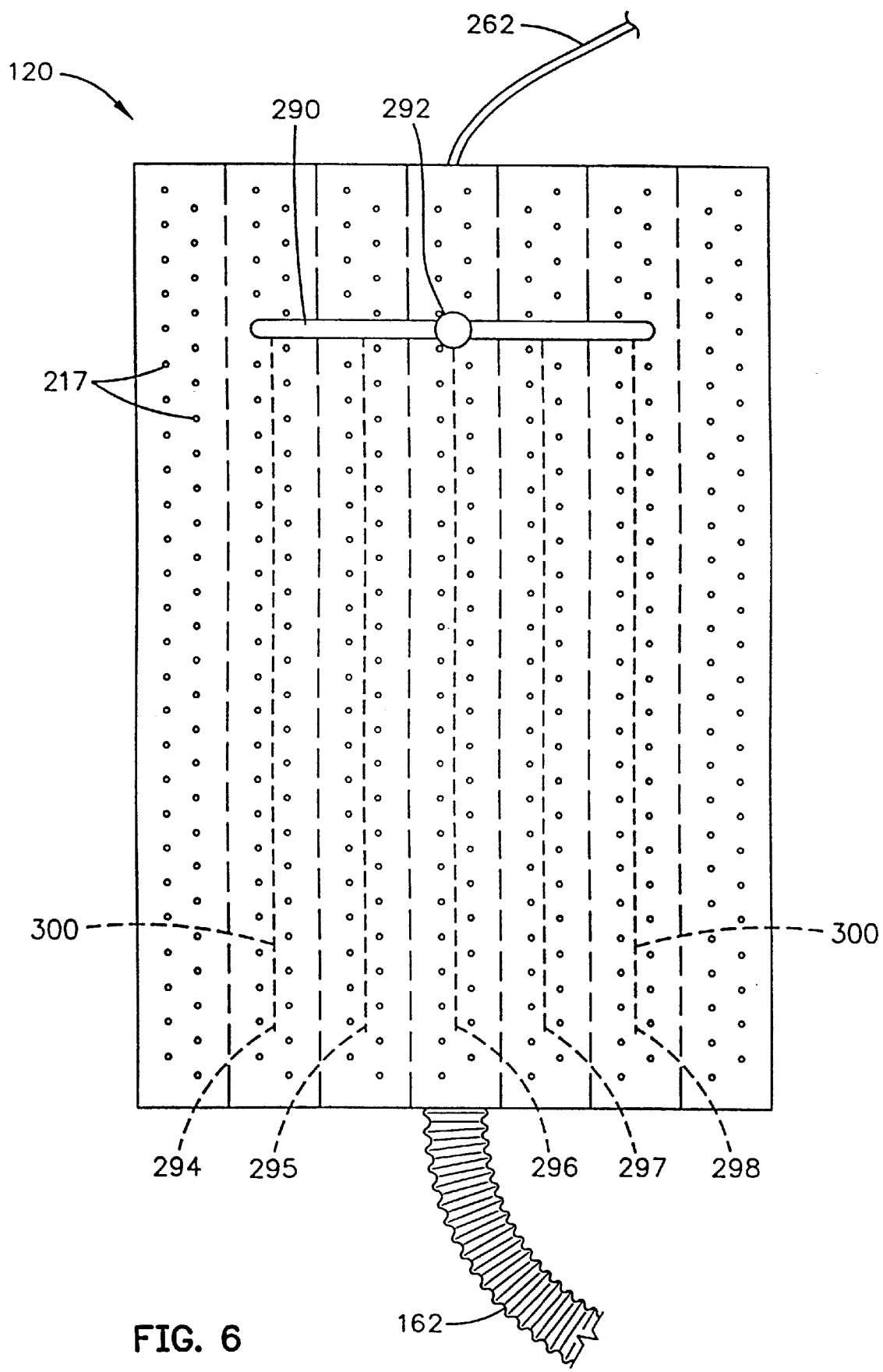
FIG. 6 is a bottom view of the inflatable thermal blanket of FIG. 1, showing another alternative two-dimensional placement for components of a fluid delivery apparatus and also showing another alternative manifold therefor.

FIG. 6 illustrates an alternative construction for an inlet manifold and fluid delivery conduits. In this construction, the inlet manifold is a linear length of tube 290 mounted to the underside of the blanket 120. The inlet line 262 extends through a hole formed in a seal, and attaches to a coupler 292 that is centrally located on the linear manifold tube 290. FIG. 6 also illustrates an alternative pattern for the conduits that deliver fluid for evaporation. In the figure, five conduits 294, 295, 296, 297 and 298, made from small bore plastic or silicone tubing, are attached at spaced locations on the linear manifold tube 290. Each of these conduits is attached to the underside of the inflatable thermal blanket 120. While the conduits are shown in a straight line pattern, it should be understood that other patterns could also be employed. In the configuration shown in FIG. 6, the orifices 300 of the fluid distribution conduits are oriented to wet the entire body of the patient 100, except the head area. It should also be understood that the conduits could be oriented to wet only selected parts of the body. As shown in FIG. 6, the numerous air apertures 217 will direct evaporative air to all portions of the patient's body where fluid is delivered by the conduits.

Figure 7:
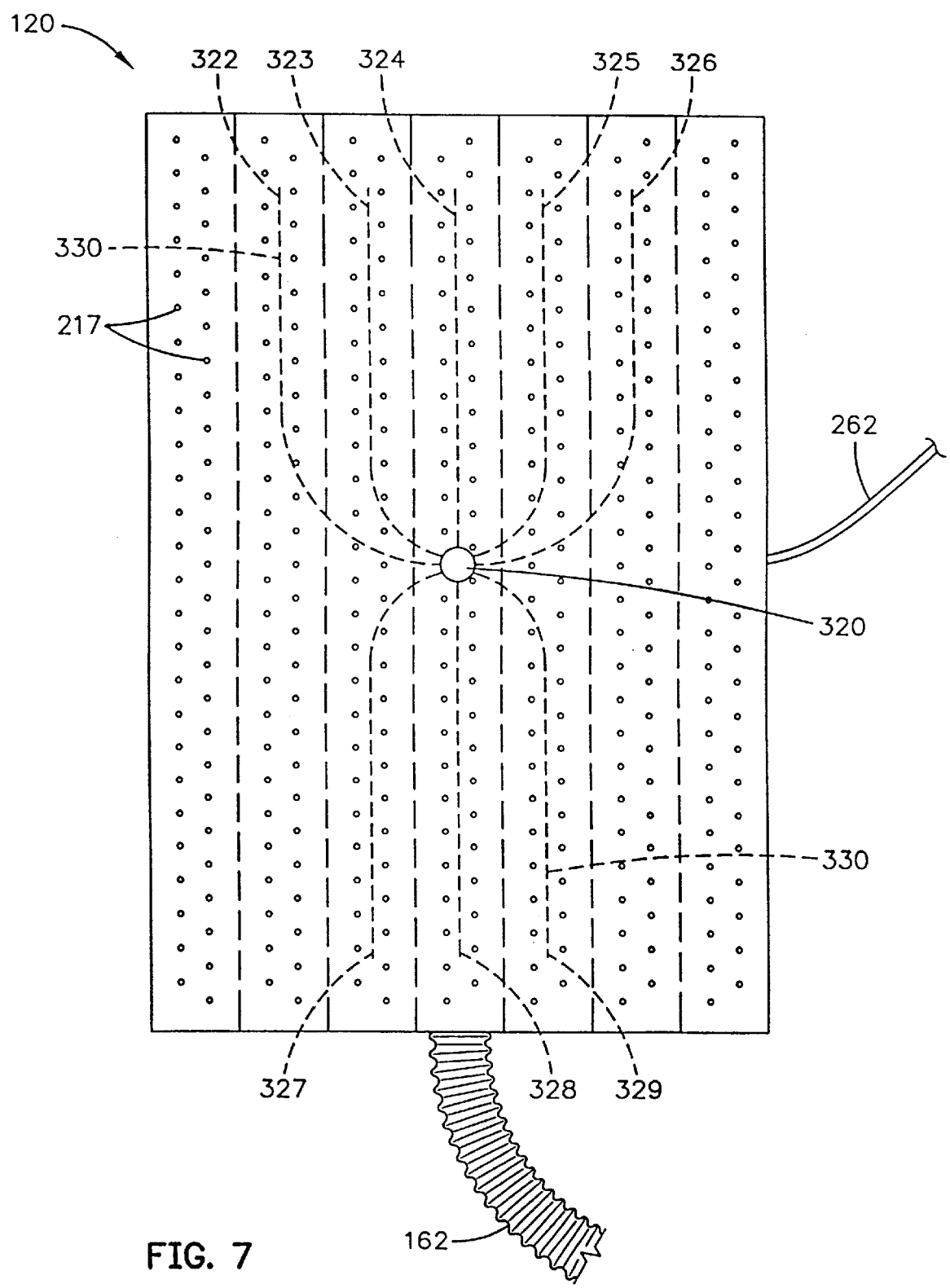
FIG. 7 is a bottom view of the inflatable thermal blanket FIG. 1, showing another alternative two-dimensional placement for components of a fluid delivery apparatus and also showing another alternative manifold therefor.

FIG. 7 illustrates another alternative construction for an inlet manifold and fluid delivery conduits. In this construction, the inlet manifold is a hub member 320 having a central fluid inlet and multiple radially oriented fluid outlets. The inlet line 262 extends through a hole formed in a central seal and attaches to a central inlet of the hub 320. FIG. 7 also illustrates an alternative pattern for the conduits in which eight conduits 322, 323, 324, 325, 326, 327, 328 and 329 made from small bore plastic or silicon tubing are attached to the radial outlets of the hub 320. Each of these conduits is attached to the underside of the inflatable thermal blanket 120. In the configuration shown in FIG. 7, the orifices 330 of the fluid distribution conduits are oriented to wet the entire body of the patient 100 except the head area. It should also be understood that the conduits could be oriented to wet only selected parts of the body. As shown in FIG. 7, the numerous air apertures 217 will direct evaporative air to all portions of the patient's body where fluid is delivered by the conduits.

The inventors contemplate modes of fluid delivery other than the tube-based embodiments that have been presented. For example, strips, or sheets, of hydrophilic material or wicking material could be used.

Figure 8:
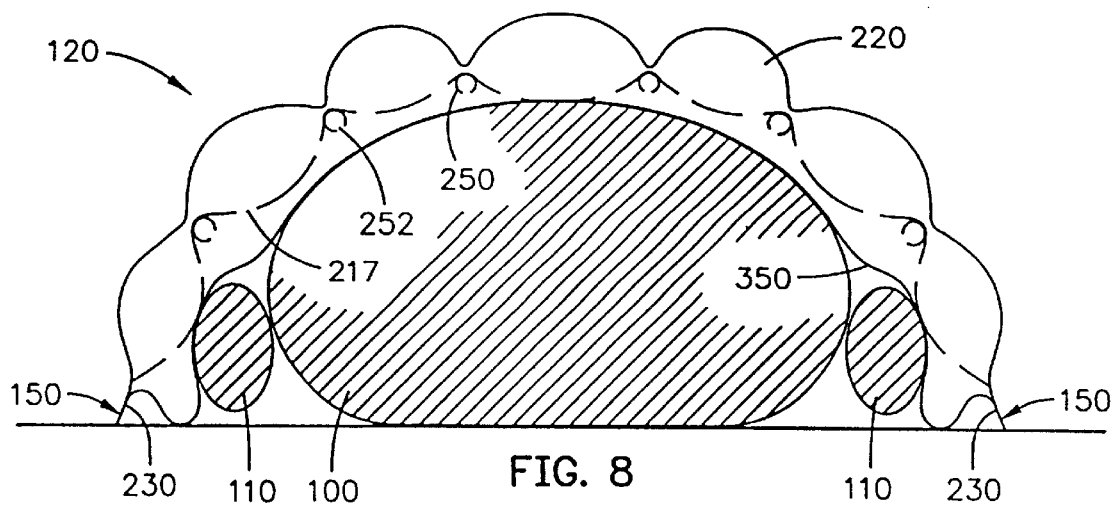
FIG. 8 is another diagrammatic cross-sectional view of the patient and inflatable thermal blanket of FIG. 1, showing additional components which may be used in the inflatable thermal blanket.

Preferably, the fluid distribution apparatus delivers the cooling fluid by depositing it directly on the skin the patient 100. However, there may be times when direct application to the skin is disadvantageous. For example, if the fluid flow rate is not adequately controlled or if the contours of the patient's body allow runoff, some of the fluid can pool under the patient. This pooling of fluid is wasteful, messy and may be harmful to the skin laying in the pooled fluid for a prolonged time. Accordingly, as shown in FIG. 8, a layer of wicking material 350 may be loosely interposed between the underside of the inflatable thermal blanket 120 and its fluid distribution system, and the skin of the patient 100. The wicking material 350 may be loosely attached to the inflatable thermal blanket 120 by connecting it at the peripheral edges only. The wicking material 350 may be any thin, loosely woven or non-woven material. One example is a single layer of cotton gauze material. The wicking material 350 serves to keep the fluid on the skin area where it is deposited, by minimizing run-off.

Figure 9:
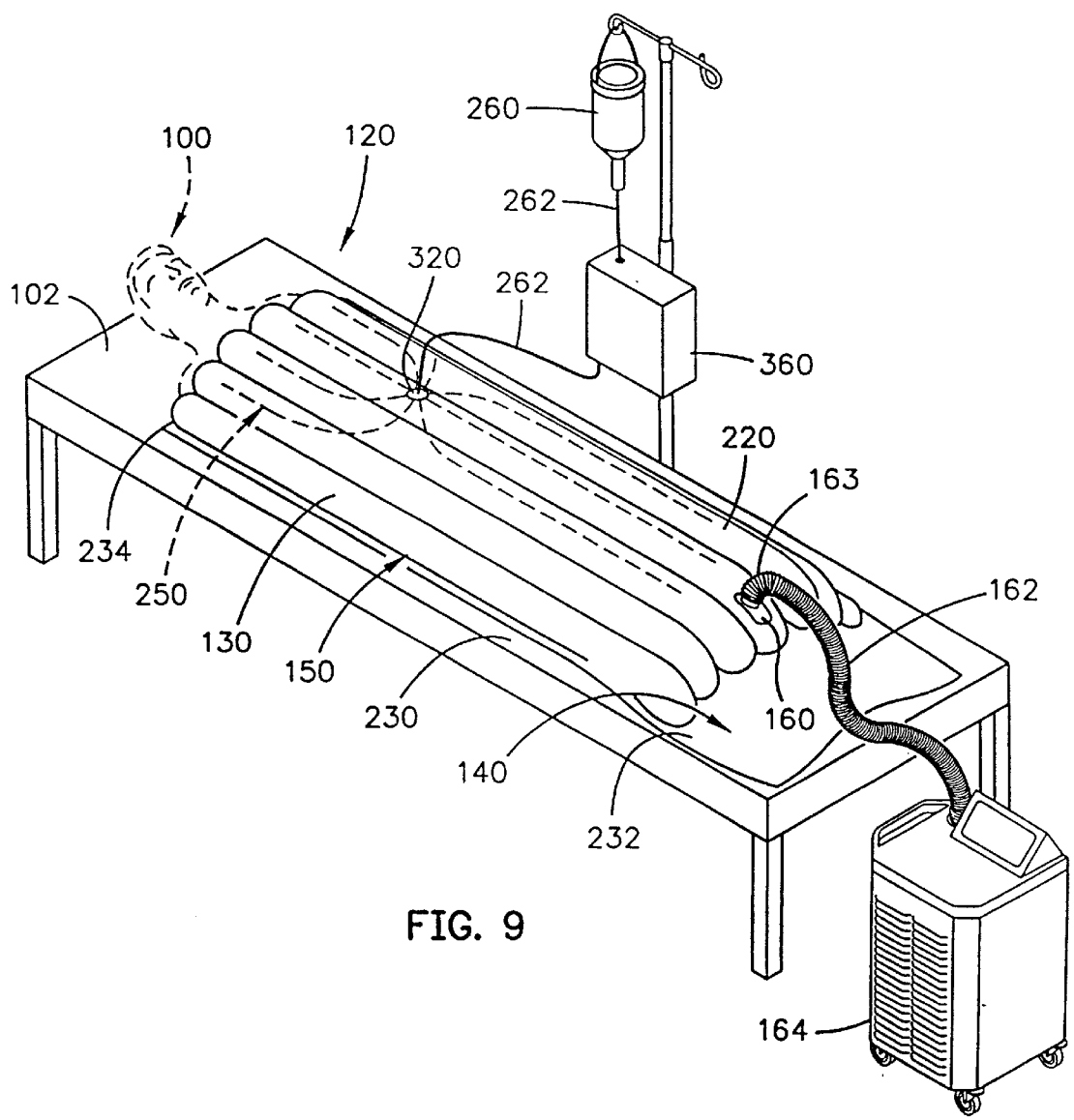
FIG. 9 is a perspective view of a patient and an inflatable thermal blanket, and also illustrates a forced-air pump for supplying air to the inflatable thermal blanket, and an alternative fluid supply apparatus for delivering an evaporative cooling fluid to the inflatable thermal blanket.

If a low fluid supply pressure is desirable, the fluid reservoir 260 can be elevated above the level of the inflatable thermal blanket 120 such that fluid pressure is venerated by gravity. This configuration is shown in FIG. 1. If higher fluid supply pressures are desired, a pump 360 may be employed, as shown in FIG. 9. The pump 360 is interposed in the fluid supply line 262. It may be provided using one of many IV fluid pumps that are generally available. Other pumps could also be employed For example, the fluid reservoir 260 could be pressurized.

Preferably, the evaporative fluid used in the fluid distribution system is water. However, other volatile fluids may also be used, or mixed with water. For example, in high humidity environments the evaporative cooling effect of water is severely reduced. In these situations, it may be desirable to use a different volatile fluid such as a mixture of alcohol and water. Other volatile, non-toxic fluids could be substituted or mixed with water to provide the desired evaporative characteristics. These fluid combinations may be premixed and supplied in sealed containers for convenience or may be mixed by the therapy provider.

Figure 10:
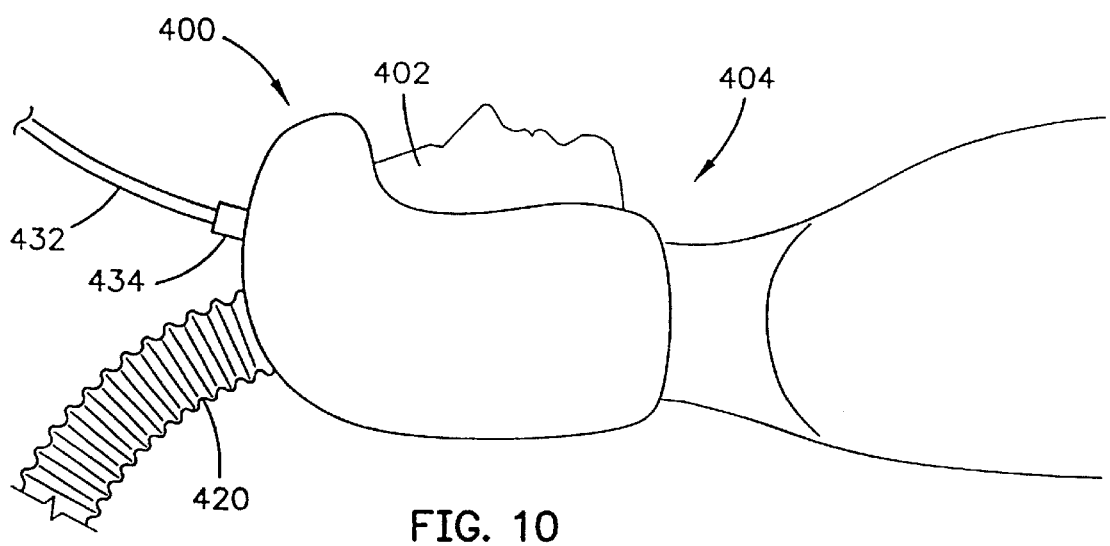
FIG. 10 is a side view of a patient and inflatable thermal blanket for convectively and evaporatively cooling a patient's head.
Figure 11:
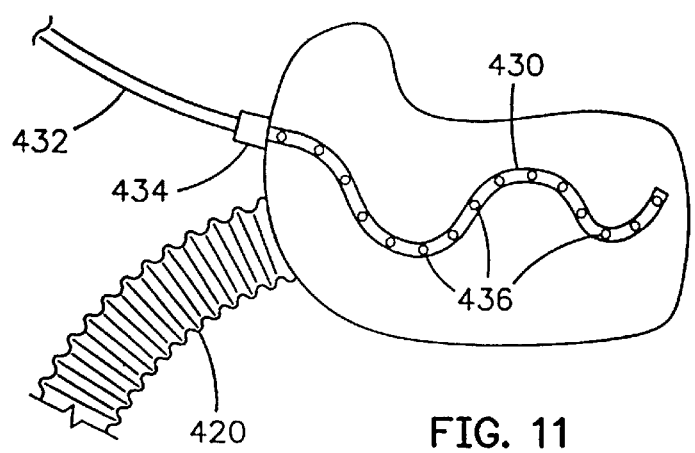
FIG. 11 is a cut-away side view of the inflatable thermal blanket of FIG. 10 showing construction details thereof.
Figure 12:
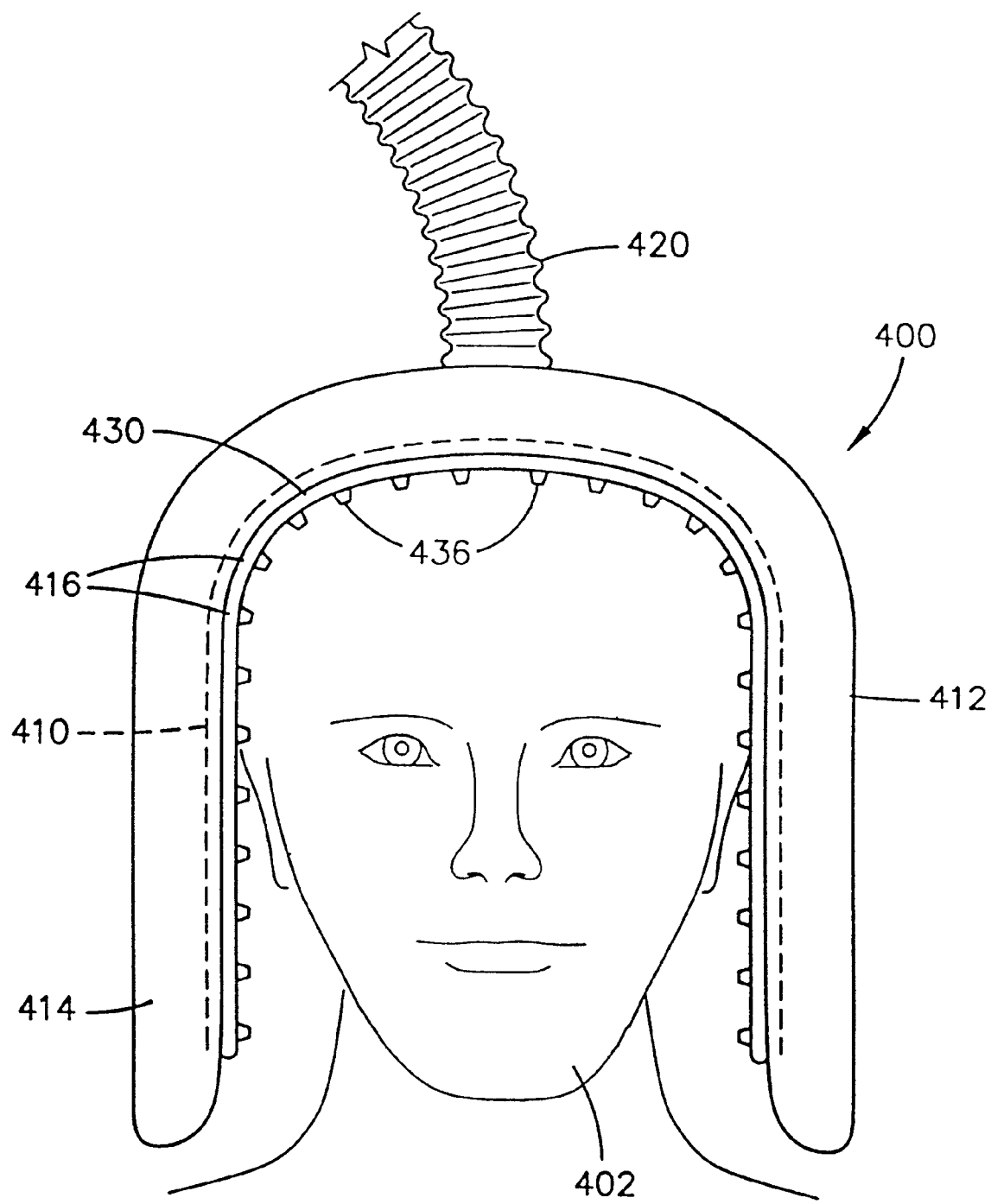
FIG. 12 is a cut-away plan view of the patient and inflatable thermal blanket of FIG. 10 showing additional construction details thereof.

In addition to inflatable thermal blankets shaped to various partial portions and combinations of the patient's trunk and limbs, specialized blanket configurations for various body parts may also be constructed. FIGS. 10, 11 and 12 illustrate an inflatable thermal blanket formed as a thermal helmet 400 constructed to fit over the head 402 of a patient 404. The helmet 400 is constructed in similar fashion to the inflatable thermal blanket 120. Thus, it has a base sheet 410 and an upper sheet 412 that are joined together by a continuous air-impervious heat seal at the periphery thereof, and optionally attached at interior portions thereof with heat seals, to define an inflatable structure 414. The base sheet 410 is provided with a plurality of apertures 416. The helmet 400 is inflated with air delivered by an airhose 420. This air is exhausted toward the patient's head 402 through the apertures 416. Thus, the helmet 400 has a component for cooling the patient 404 convectively. It also has an evaporative component that includes a conduit 430 made from small bore plastic tubing or the like. The conduit 430 is attached to the underside of the helmet 400, and is arranged in serpentine fashion. The conduit 430 extends through a hole in the helmet 400, and connects to an inlet line 432 via a connector 434. The inlet line 432 is connected to a fluid supply reservoir (not shown), and delivers a cooling fluid to the conduit 430. The conduit 430 is provided with multiple orifices 436, shown in FIG. 12 as spray nozzles. Alternatively, slits or holes could also be used to provide the orifices.

Advantageously, the regions of the patient's body that receive the combined evaporative-convective cooling in accordance with the invention can be selected by the care giver. The volume of fluid delivered can be controlled to either be fully evaporated, or to be in excess, and thus be delivered to body areas which are at various distances from the orifices. Optionally, an incorporated liquid sensing device could be used to determine and control the rate of delivery of the fluid for evaporation.

The fluid distribution apparatus thus allows fluid to be distributed and delivered to desired portions of the patient's body, at a controlled rate, over a prolonged period of time, without requiring the inflatable thermal blanket to be lifted or frequent operator involvement. While the inflatable thermal blankets illustrated herein are shown in particular shapes and sizes, it will be recognized that because different patients have different shapes and sizes, different shapes and sizes of inflatable thermal blankets may be made available to accommodate most patients.

Other embodiments and modifications of this invention may occur to those of ordinary skill in the art in view of these teachings. Therefore, this invention is to be limited only by the following claims, which include all such embodiments and modifications when viewed in conjunction with the above specification and accompanying drawings.

What is claimed is:

1. An apparatus for cooling a patient's head, comprising:
   an upper sheet and a base sheet connected together at a plurality of locations to form a convective device adaptable to the patient's head;
   an air inlet in the convective device for delivering pressurized air;
   a plurality of apertures opening through the base sheet for exhausting the pressurized air from the convective device toward the patient's head; and
   an evaporative cooling element adapted to be disposed beneath the base sheet.

2. The apparatus of claim 1, wherein the evaporative cooling element includes one or more conduits, a fluid inlet connected to one or more conduits, and a plurality of orifices in the one or more conduits.

3. The apparatus of claim 2, wherein the conduits comprise plastic tubing.

4. The apparatus of claim 2, wherein the conduits comprise silicone tubing.

5. The apparatus of claim 2 wherein the orifices are holes in the conduits.

6. The apparatus of claim 2 wherein the orifices are slits in the conduits.

7. The apparatus of claim 2 wherein the orifices are nozzles on the conduits.

8. The apparatus of claim 2, wherein the orifices are holes in the ends of the conduits.

9. The apparatus of claim 2, wherein the fluid inlet is a distribution manifold that connects to multiple ones of the conduits.

10. The apparatus of claim 2, further including wicking material adapted to be disposed against the evaporative cooling element.

11. The apparatus of claim 10, wherein the layer of wicking material is made from a woven material.

12. The apparatus of claim 10, wherein the layer of wicking material is made from a non-woven material.

13. The apparatus of claim 10, wherein the wicking material is loosely attached to the convective device.

14. A system for cooling a patient's head, comprising:
   a source of a flow of temperature-controlled air;
   a convective device adaptable to the patient's head including an upper sheet and a base sheet connected together at a plurality of locations;
   an air inlet in the convective device for delivering a flow of temperature-controlled air into the convective device;
   an airhose connecting the air source to the air inlet;
   the base sheet including means for exhausting temperature-controlled air from the convective device to convectively cool the patient's head; and
   an evaporative cooling element adapted to exhaust fluid to evaporatively cool the patient's head.

15. The system of claim 14, wherein the evaporative cooling element includes one or more conduits and one or more orifices in each of the one or more conduits.

16. The system of claim 15, wherein the conduits comprise plastic tubing.

17. The system of claim 15, wherein the conduits comprise silicone tubing.

18. The system of claim 15 wherein the orifices are holes in the conduits.

19. The system of claim 15 wherein the orifices are slits in the conduits.

20. The system of claim 15 wherein the orifices are nozzles on the conduits.

21. The system of claim 15, wherein the orifices are holes in the ends of the conduits.

22. The system of claim 15, wherein the delivery apparatus includes a fluid inlet comprising a distribution manifold that connects to multiple ones of the conduits.

23. The system of claim 15, further including wicking material adapted to be disposed against the evaporative cooling element.

24. The system of claim 23, wherein the wicking material is made from a woven material.

25. The system of claim 23, wherein the wicking material is made from a non-woven material.

26. The system of claim 23, wherein the wicking material is attached to the convective device.

27. The system of claim 15, further including a fluid reservoir connected to the evaporative cooling element and positioned above the convective device to supply fluid via gravity feed.

28. The system of claim 15, further including a fluid reservoir and a pump connected between the evaporative cooling element and the fluid reservoir to supply fluid via mechanical pressurization.

29. The system of claim 15, wherein the fluid is water.

30. The system of claim 15, wherein the fluid is a volatile liquid.

31. The system of claim 14, wherein the means include apertures through the base sheet.

32. A method for convectively and evaporatively cooling a patient's head with a convective system, the convective system including:
   a source of a flow of temperature-controlled air;
   a convective device adaptable to the patient's head;
   an inlet for delivering the flow of temperature-controlled air into the convective device;
   an airhose connecting the source to the inlet;
   means for exhausting temperature-controlled air from the convective device;
   a fluid reservoir; and
   an evaporative cooling element adapted to exhaust fluid;
   the method including:
      placing the convective device adjacent the patient's head;
      providing a flow of temperature-controlled air into the convective device;
      providing a fluid to the evaporative cooling element;
      convectively cooling the patient's head by exhausting air from the convective device; and
      evaporatively cooling the patient's head by exhausting the fluid from the evaporative cooling element.

33. The system of claim 14, wherein the temperature-controlled air is cooled air.

34. The system of claim 14, wherein the temperature-controlled air is dehumidified air.

35. A system for cooling a patient's head, comprising:
   a convective device with a base sheet adaptable to the patient's head;
   an evaporative cooling element disposed against the base sheet; and
   means for delivering fluid from the evaporative cooling element onto the patient's head.

36. The system of claim 35, wherein the evaporative cooling element is attached to the base sheet.

37. The system of claim 35, wherein the means for delivering fluid are orifices in the evaporative cooling element.

38. The system of claim 35, wherein the means for delivering fluid are nozzles in the evaporative cooling element.

39. A method for convectively cooling a patient's head with a convective system, the convective system including:
   a source of a flow of temperature-controlled air;
   a convective device adaptable to the patient's head;
   an inlet for delivering the flow of temperature-controlled air into the convective device;
   an airhose connecting the source to the inlet; and
   means for exhausting temperature-controlled air from the convective device;
   the method including:
      placing the convective device adjacent the patient's head;
      providing a flow of temperature-controlled air into the convective device; and
      convectively cooling the patient's head by exhausting air from the convective device.

40. The method of claim 39 further including evaporatively cooling the patient's head with the convective system, the convective system further including:
   a source of fluid; and
   an evaporative cooling element adapted to exhaust fluid;
   the method further including:
      providing a fluid to the evaporative cooling element; and
      evaporatively cooling the patient's head by exhausting the fluid from the evaporative cooling element.

* * * * *